United States Patent [19]

Krenitsky et al.

[11] 4,097,337

[45] Jun. 27, 1978

[54] BACTERIAL CULTURE MEDIUM

[75] Inventors: Thomas Anthony Krenitsky, Chapel Hill; Stanley Robert Morris Bushby, Durham, both of N.C.

[73] Assignee: Burroughs Wellcome Co., Research Triangle Park, N.C.

[21] Appl. No.: 652,770

[22] Filed: Jan. 27, 1976

[30] Foreign Application Priority Data

Jan. 27, 1975   United Kingdom ................ 3445/75

[51] Int. Cl.² ............................................... C12K 1/10
[52] U.S. Cl. ............................ 195/100; 195/103.5 K
[58] Field of Search ............... 195/100, 101, 102, 103, 195/99

[56] References Cited

PUBLICATIONS

The European Journal of Biochemistry, vol. 21, pp. 191-198; 1971.
Chemical Abstracts, vol. 85, 117418p; 1976.

*Primary Examiner*—Alvin E. Tanenholtz
*Assistant Examiner*—Robert J. Warden
*Attorney, Agent, or Firm*—Donald Brown

[57] ABSTRACT

A bacterial culture medium used in testing for the susceptibility of bacteria to anti-folate, anti-bacterial agents is substantially improved for this use by the incorporation therein of purified thymidine phosphorylase of bacterial origin.

7 Claims, No Drawings

BACTERIAL CULTURE MEDIUM

This invention relates to culture media for microbes and in particular to culture media used in testing for the susceptibility of bacteria to anti-folate anti-microbial agents such as sulphamethoxazole (SMX) and/or trimethoprim (TMP).

It has been known for a number of years that culture media in common use are often unsuitable for determining sensitivity of bacteria to sulphonamides or trimethoprim, i.e. agents interfering with the synthesis of folates in these organisms. This unsuitability manifests itself by giving long tailing end-points when the serial dilution method is used and by partial growth within the inhibition zones when the diffusion method is employed. It has been shown by Bushby (*Med. J. Aust. Special Supplement* (1973) 1: 10) and Koch and Burchall (*Applied Microbiology* (1971) 22: 812) that thymidine is a very potent reversing agent of the inhibiting activities of sulphonamides and trimethoprim.

In 1945 Harper and Cawston (*J. Path. Bact.*, 57: 59) showed that when lysed horse blood was added to a poor susceptibility test medium, it could convert this into a satisfactory one. Since this early work, and that of several other workers, it has become common practice to include lysed horse blood in antibacterial susceptibility test media, in order to reduce the partial growth often observed within the inhibition zones produced by sulphonamides. More recently this method has also been shown to be similarly effective in testing with respect to trimethoprim (Bushby, *Postgraduate Med. J.* (1969) 45: 10; and Darrell et al., J. Clin. Path, (1968) 21: 202).

Harper and Cawston established that (a) lysed horse blood was more effective than whole blood in neutralizing sulphonamide-antagonizing substance(s), (b) blood of several other species was inactive, (c) the activity of the lysate increased with incubation time and temperature (up to 30°) and (d) the lysate did not effect the reversal of sulphonamide-inhibition by p-aminobenzoic acid. They concluded that the lysed blood contained a factor which neutralizes sulphonamide-antagonizing substance(s).

This so-called Harper-Cawston Factor is effective only with media which contain a moderate level of thymidine, i.e. from about 0.1 to 15 $\mu$g/ml. Below 0.1 $\mu$g/ml the activity of the drugs is not antagonized; thus, removal of such a small amount of thymidine has no effect on the drug inhibition observed. At very high levels of thymidine, i.e. greater than 15 $\mu$g/ml, the activity of Harper-Cawston Factor is not sufficient to overcome the reversal of the activities of the sulphonamides and trimethoprim, possibly because the high concentration of thymine, produced as a result of the cleavage of thymidine, can replace the much more active thymidine in the reversal.

The Harper-Cawston Factor has been reported to be thymidine phosphorylase (Bushby in *Trimethoprim/Sulfamethoxazole in Bacterial Infections: A Wellcome Foundation Symposium.* Ed Bernstein & Salter, Churchill Livingston, Edinburgh & London, 1973, p. 31-38; and Bushby, *Med. J. Aust. Special Supplement*, 1973, 1: 10-18) It has been pointed out in the latter reference that "although thymidine interferes with the in vitro activity of TMP/SMX, it is not usually present in animals in sufficiently high concentrations to affect the in vivo activity."

One disadvantage of including lysed horse blood in a culture medium is that it imparts a reddish brown color to the medium; the greater the amount of horse blood, the deeper the color. This coloration is undesirable since it greatly interferes with the assessment of bacterial growth after incubation. For example, in the case of fluid media the increased color decreases the transparency of the media making optical density measurements far less accurate. with solid media there is a decrease in contrast of the agar making it more difficult to precisely measure inhibition zone sizes and to determine the presence or absence of partial growth within the zones of inhibition. Furthermore the requirement of the addition of lysed horse blood to bacterial culture media means that the media are virtually impossible to define, a somewhat undesirable characteristic. A further disadvantage of using horse blood is that it is commercially available in very limited supply and from ony a very few suppliers world-wide.

It has recently been found that the addition of the isolated and purified enzyme thymidine phorphorylase of bacterial origin, to a wide variety of commonly used growth media, improves those media for susceptibility testing of bacteria to anti-folate drugs.

According to one aspect of the invention there is provided a composition for testing the susceptibility of bacteria to anti-folate drugs which comprises a bacterial growth medium in combination with purified thymidine phosphorylase of bacterial origin.

Addition of the enzyme thymidine phosphorylase improves many media for susceptibility testing of bacteria to anti-folate drugs, such as sulphamethoxazole and trimethoprim, for example Mueller-Hinton Broth and Agar, Oxoid Sensitivity Test Broth and Agar, Wellcotest Sensitivity Test Agar, Brain Heart Infusion Broth and Agar, and Typtone Soya Agar.

Thymidine phosphorylase has previously been purified from bacteria such as *Salmonella typhimurium, Bacillus cereus, Bacillus stearothermophilus & Haemophilus influenzae* and particularly from a strain of *Escherichia coli* requiring thymine and methionine for growth. This latter purification involved an extremely lengthy process consisting of precipitation, fractionation, several chromotographic steps and dialysis (Schwartz, M., 1971, Eur. J. Biochem. 21: 191-198). The enzyme preparation recovered from this process, however, was only 25-fold purer than the crude cell extract.

It has recently been found that certain strains of bacteria, in particular a certain strain of *E. coli*, produce inordinate amounts of thymidine phosphorylase under appropriate growth conditions and that this enzyme may be isolated and purified by applying the cell extract to specific adsorbents and eluting it therefrom to give a much higher yield of a much purer preparation than has heretofore been achieved. Moreover, this new isolation/purification procedure is adpatable to large scale production of the enzyme.

According to a second aspect of the invention there is provided a process for preparing purified thymidine phosphorylase of bacterial origin, which process comprises the steps of extracting the crude enzyme from bacteria into an aqueous medium, and subjecting the extract to a fractionation procedure which includes adsorption, chromatographic and dialysis steps. This process is characterized in that (1) a strain of bacteria is selected which has the capability of producing high concentrations of thymidine phosphorylase under appropriate growth conditions and (2) the crude cell extract obtained therefrom is applied to a calcium phosphate gel absorbent containing substantially equivalent amounts of $Ca^{++}$ and $PO_4\equiv$, preferably as a first step in purification. Preferably, the eluant is subsequently contacted with DEAE cellulose and/or cellulose-epichlorohydrin triethanolamine (ECTEOLA-cellulose), with dialysis against water or a suitable buffer being carried out after elution from DEAE-cellulose and before adsorption of ECTEOLA-cellulose.

*Escherichia coli* B-96 (ATCC 13473) is eminently advantageous for the purposes of the present invention. *Salmonella typhimurium* LT-2 (ATCC 15277) is an example of another strain of bacteria which produces large amounts of thymidine phosphorylase and thus is useful in the practice of this invention. In certain cases, where a more thermostable enzyme is desirable, the enzyme isolated from B. stearothermophilus has proven effective.

The *E. coli* strain ATCC 13473 may be cultured in a minimal salts medium containing a suitable carbon source and additional purines. Alternatively, the bacteria may be cultured in a yeast extract medium. A crude extract of the enzyme may then be made by sonication of the bacterial cells in phosphate buffer followed by centrifugation to remove the cell debris.

The crude extract is for instance admixed with a small amount of calcium phosphate gel and then centrifuged to remove unwanted protein. The supernatent so obtained may then be admixed with a further aliquot of calcium phosphate gel and the enzyme absorbed thereto. The enzyme activity may be eluted from the gel by sequential washings with phosphate buffer. The enzyme may be adsorbed of DEAE-cellulose, washed and eluted therefrom. After dialysis, the preparation may be adsorbed to ECTEOLA-cellulose and eluted therefrom.

Monitoring of the elutions for enzyme activity, at all stages of the purification, may conveniently be carried out using a spectrophotometric assay at a selected wavelength.

The enzyme so purified can be conveniently made available as a suspension in aqueous ammonium sulphate.

The enzyme is also present in a number of vertebrate tissues and can be purified therefrom, but the levels in mammalian tissues are generally much lower than in bacteria. Furthermore purified microbial thymidine phosphorylase is many times more active than the purified mammalian counterpart.

Indeed horse blood has been found to contain about 40 to 100 units of thymidine phosphorylase activity (as defined herein) per ml. The *E. coli* sonicate of Example 1 contains greater than 1000 times this concentration. Thus, the advantages of an economical method of preparing the purified enzyme from a bacterial source are many and significant. Not only is there a more readily available, inexpensive source of the enzyme, but the process for extracting and purifying it is much more economical.

The concentration of thymidine phosphorylase incorporated into the media is preferably in the range of about 2 to 200 units of enzyme activity/ml of medium, more preferably between 5 and 100 units/ml and most preferably between 7 and 50 units/ml. One unit of enzyme activity of purified enzyme is that amount of the enzyme which catalyzes the formation of one nanomole of thymine/minute from a one millimolar solution of thymidine at 25° C in the presence of 200mM potassium phosphate buffer at pH 7.4.

Media, to which purified thymidine phosphorylase has been added, may be suitable for testing the susceptibility to anti-folate drugs of a variety of organisms, such as *Streptococcus pyogenes, Staphylococcus aureus, Vibrio comma, Erysipelothrix rhusiopathiae, Serratia marcescens, Klebsiella pneumoniae, Kleb. aerogenes, Sal. typhosa, E. coli, Shigella flexneri, Shig. dysenteriae, Enterobacter aerogenes, Entero. cloacae, Citrobacter freundii, Proteus vulgaris, Pr. mirabiles, Pr. rettgeri,* and *Pseudomonas aeruginosa. Strep. faecalis* is an outstanding exception, because with this organism, thymine is as effective as is thymidine in virtually reversing the activity of inhibitors of folate reductase, eg. trimethoprim.

The purified enzyme may be added to the desired medium at any suitable stage of manufacture or preparation. For example, it may be added aseptically as a sterile solution after autoclaving of the medium, and when the temperature has dropped to about 50°–55° C. After the enzyme has been added, the medium should be processed as soon as possible so that the enzyme-treated medium is not maintained at 50°–55° C. for more than about 5–10 minutes in order to minimise inactivation of the enzyme.

According to the present invention, in a third aspect there is provided a method of preparing a composition suitable for testing the susceptibility of bacteria to antifolate drugs which comprises the admixture of a purified preparation of thymidine phosphorylase of bacterial origin with a bacterial growth medium.

One particular advantage of the composition so produced is that is is light colored and transparent, which facilitates the accurate evaluation of bacterial growth in the determination of bacterial sensitivity to antifolate drugs.

According to yet another aspect of the invention there is provided a stabilized thymidine phosphorylase preparation containing ammonium sulfate. The formulation of increased stability may be suspension of the enzyme in an ammonium sulfate solution.

It is known in the prior art that thymidine phosphorylase of bacterial origin is stable at $-20°$ C. but that at 4° C. activity decreases at a significant rate. It has now been found that formulations of the purified enzyme can be made remarkably stable to decomposition by adding ammonium sulfate to the preparation provided that the protein content of the preparation is at least 5mg protein/ml. The protein content need not necessarily all consist of the enzyme. Concentrated solutions of the enzyme (5mg protein/ml or greater) in phosphate buffer containing 10% ammonium sulfate, for example, may be stored for long periods of time with little or no loss of activity. Stable suspensions of thymidine phosphorylase in aqueous ammonium sulfate may also be prepared.

The following examples illustrate the invention but do not limit it in any way.

EXAMPLE 1

Thymidine Phosphorylase Purification

*E. Coli* B-96 (ATCC 13473) was grown in aerated vessels at 34° C in a minimal salts medium containing $Na_2HPO_4$ (18.9 g/1), $KH_2PO_4$ (6.3 g/1), $MgSO_4 \cdot 7H_2O$ (0.2 g/1), $(NH_4)_2SO_4$ (2.0 g/1), adenosine (0.5 g/1), and casamino acids (8.0 g/1). The cells were harvested by centrifugation when the optical density of the culture at 600 nm (without dilution) reached 2.0. The following operations were carried out at 3° C unless otherwise specified. The cell paste (25 g) was suspended in two times its weight of 5 mM potassium phosphate buffer, pH 8.0 (Buffer A). The cell suspension was sonicated in 5 ml aliquots, each for two 12 second periods with a 50 second cooling interval. A Branson Model 5125 Sonic Oscillator was used at a power setting of six. The sonicates were pooled and centrifuged for 20 minutes at 48,000 × g. To the supernatant (Stage I - see Table I below) was slowly added 25 ml of a calcium phosphate gel suspension (31 mg dry solid per ml, aged at 3° C for 5 months). The resulting suspension was stirred for 10 minutes and then centrifuged at 12,000 × g for 5 minutes. The supernatant was mixed with an additional 100 ml of the calcium phosphate gel suspension, and the mixture was stirred for 10 minutes and centrifuged at 9,700 × g for 15 minutes. The resulting gel pellet was washed with Buffer A (100 ml) by resuspension and centrifugation at 9,700 × g for 15 minutes.

The enzyme activity was eluted from the gel pellet by two sequential washings; the first with 10 mM potassium phosphate buffer, pH 8.0 (100 ml) and the second with 20 mM potassium phosphate buffer, pH 8.0 (100 ml). The two washes were combined (Stage II).

The remainder of the procedure was carried out at 25° C. The combined washes were applied to DEAE-cellulose column, 1.8 cm in diameter by 6 cm high, which was previously equilibrated with 20 mM potassium phosphate, pH 6.4 (Buffer B). The loaded column was washed with Buffer B (100 ml), and the enzyme was then eluted with a linear gradient of phosphate buffer. This gradient was prepared by adding with thorough mixing 200 mM potassium phosphate buffer, pH 6.4 (200 ml) to a mixing chamber, which was originally filled with Buffer B (200 ml), at such a rate as to maintain constant volume within the mixing chamber. The fractions containing the highest enzyme activity were pooled (Stage III) and dialyzed using a cellulose dialyzer tubing (¼ inch diameter) against water (2 l) for 1 hour. The dialysis was repeated, and then the dialysate was applied to an ECTEOLA-cellulose column (1.8 × 5 cm) previously equilibrated with Buffer A. The loaded column was washed with Buffer A (100 ml). The enzyme was then eluted with a linear gradient eluant prepared as above using a mixing reservoir initially filled with Buffer A (200 ml) into which 200 mM potassium phosphate buffer, pH 8.0 (200 ml) was siphoned by gravity as the column solution proceeded. The fractions containing enzyme activity were pooled (Stage IV) and sufficient ammonium sulfate added to give a suspension of the enzyme in 80% ammonium sulfate solution. This overall procedure resulted in a 100-fold increase in specific activity with respect to protein and the virtually complete removal of nucleic acids.

Thymidine phosphorylase activity was assayed spectrophotometrically by measuring the decrease in absorbance at 290 nm accompanying the phosphorolysis of thymidine to thymine. At 290 nm and pH 7.4 thymidine has a higher extinction coefficient than thymine ($\Delta\epsilon = -480 M^{-1} cm^{-1}$) The assay mixture contained 200 mM potassium phosphate buffer, pH 7.4 and 1 mM thymidine in a total volume of 2.5 ml. One unit of enzyme activity is that amount which catalyzes the formation of one nanomole of thymine per minute from thymidine at 25° C.

Table I summarizes the results of the purification described in this example. This procedure has been scaled up 60-fold with similar results.

TABLE I:
Purification of Thymidine Phosphorylase from Escherichia coli B-96

| Procedure | Stage No. | Vol. (ml) | Activity Units ml | Total Units | Protein mg/ml | Activity Units mg prot. | Yield % | Purification -fold |
|---|---|---|---|---|---|---|---|---|
| Sonicate Supernatant | I | 65.5 | 106,000 | 6,943,000 | 40 | 2,650 | 100 | — |
| Eluate from Calcium Phosphate Gel | II | 206 | 27,600 | 4,685,600 | 0.99 | 27,880 | 82 | 11 |
| DEAE-cellulose Eluant | III | 52 | 80,500 | 4,186,000 | 0.61 | 132,000 | 60 | 50 |
| ECTEOLA-cellulose Eluant | IV | 66 | 50,700 | 3,346,200 | 0.19 | 266,800 | 48 | 101 |

EXAMPLE 2

Solid Medium

Mueller-Hinton (Difco) Agar was prepared in the normal manner and autoclaved. After the medium had been removed from the autoclave and allowed to cool to 50°-55° C, a sterile solution of purified thymidine phosphorylase as prepared in Example 1 containing sufficient enzyme to give a final concentration of 40 units of the purified enzyme per ml of medium, was added aseptically. The medium was thoroughly mixed, poured into sterile Petri dishes and allowed to cool to room temperature.

EXAMPLE 3

Sensitivity Testing

Mueller-Hinton Agar (Wilson) and Brain-Heart Infusion Agar (Difco) were prepared in the normal manner and autoclaved (three batches of each). After removal from the autoclave, one batch of each medium was poured into sterile Petri dishes. The other two batches of each medium were allowed to cool to 55° C. To one batch of each was then added sufficient lysed horse blood to give a final concentration of 5%, and to the final batch of each medium was added a sterile solution of thymidine phosphorylase sufficient to give a final concentration of 40 units/ml. Each batch was thoroughly mixed and then poured into sterile Petri dishes. After cooling to room temperature, each agar plate was seeded with 2 ml of a diluted ($10^{-4}$) overnight broth culture (Mueller-Hinton broth) of E. coli. Excess fluid was removed, and the plates were allowed to dry. Filter paper discs containing 1.25 mg TMP, 1.25 mg TMP = 23.75 mg SMX, and 23.75 mg SMX were then placed on the surface of the plates, which were then incubated at 37° C for 16 hours giving a lawn of not quite confluent growth. The zones of inhibition were determined and expressed as the distance from the edge of the disc to the edge of the growth of uninhibited colonies. Table II summarizes the results.

TABLE II:

Sensitivity Testing Size of Zone in mm

| Medium | Reversing Agent | TMP 1.25 μg | SMX 23.75 μg | TMP 2.36 1.25 μg + SMX 23.75 μg |
|---|---|---|---|---|
| Brain-Heart Infusion Agar (Difco) | Thymidine Phosphorylase 40 Units/ml | 22(25) | 17(20) | 26(31) |
|  | Lysed Horse Blood 5% | 14(22) | 12(20) | 21(29) |
|  | Nil | (22) | (23) | (31) |
| Mueller-Hinton Agar (Wilson) | Thymidine Phosphorylase 40 Units/ml | 24(27) | 24(26) | 32(36) |
|  | Lysed Horse Blood 5% | 25(28) | 24(26) | 31(35) |
|  | Nil | (25) | (26) | (35) |

( ) Includes zone of partial inhibition.

Mueller-Hinton agar is improved for sensitivity testing to about the same degree by the addition of bacterial thymidine phosphorylase as by the addition of lysed horse blood. However, the enzyme improves Brain-Heart Infusion agar significantly more effectively than does lysed horse blood. In addition, the virtually colorless plates produced according to this invention were read and evaluated much more easily and quickly than the colored horse blood plates.

We claim:

1. A composition which is usable for testing the susceptibility of bacteria to anti-folate agents comprising a bacterial growth medium in combination with purified thymidine phosphorylase enzyme of bacterial origin wherein the concentration of thymidine phosphorylase enzyme in the growth medium is from 2 to 200 units of enzyme activity/ml of medium.

2. A composition as claimed in claim 1 wherein the concentration is from 5 to 100 units/ml.

3. A composition as claimed in claim 1 wherein the concentration is from 7 to 50 units/ml.

4. A composition as claimed in claim 1 wherein the thymidine phosphorylase is obtained from an *Escherichia coli* strain.

5. A composition as claimed in claim 4 wherein the strain of *E. coli* is B-96 (ATCC 13473).

6. A composition as claimed in claim 1 wherein the bacterial growth medium is Mueller-Hinton Broth, Mueller-Hinton Agar, Oxoid Sensitivity Test Broth, Oxoid Sensitivity Test Agar, Wellcotest Sensitivity Test Agar, Brain Heart Infusion Broth, Brain Heart Infusion Agar or Tryptone Soya Agar.

7. A method of preparing a composition comprising a bacterial growth medium and thymidine a bacterial growth medium and thymidine phosphorylase of bacterial origin wherein the concentration of thymidine phosphorylase enzyme in the growth medium is from 2 to 200 units of enzyme activity/ml of growth medium which comprises mixing a bacterial growth medium with a sufficient amount of thymidine phosphorylase enzyme of bacterial origin/ml of bacterial growth medium which is usable for testing the susceptibility of bacteria to antifolate agents to produce 2 to 200 units of enzyme activity/ml of bacterial growth medium.

* * * * *